US005945523A

United States Patent [19]

Ullrich et al.

[11] Patent Number: 5,945,523

[45] **Date of Patent: *Aug. 31, 1999**

[54] DIAGNOSIS AND TREATMENT OF TKA-1 RELATED DISORDERS

[75] Inventors: Axel Ullrich, München, Germany; Klaus Seedorf, Vedback, Denmark

[73] Assignee: Max-Planck-Gesellschaft zur Forderung der Wissenschaften E.V., Munich, Germany

[ * ] Notice: This patent is subject to a terminal disclaimer.

[21] Appl. No.: 08/732,870

[22] Filed: Oct. 15, 1996

Related U.S. Application Data

[63] Continuation-in-part of application No. 08/666,067, Jun. 14, 1996, and application No. 08/665,037, Jun. 13, 1996

[60] Provisional application No. 60/005,423, Oct. 13, 1995, and provisional application No. 60/005,167, Oct. 13, 1995.

[51] Int. Cl.[6] .................................................... C12N 15/12

[52] U.S. Cl. .................... 536/23.5; 536/24.31; 435/69.1; 435/252.3; 435/254.11; 435/320.1; 435/325; 435/194

[58] Field of Search ................................. 536/23.5, 23.1, 536/24.31; 435/325, 252.3, 254.11, 320.1, 69.1, 194

[56] References Cited

U.S. PATENT DOCUMENTS 4,945,050 7/1990 Sanford et al. ...................... 435/172.1

FOREIGN PATENT DOCUMENTS 9213001 8/1992 WIPO .
9506735 3/1995 WIPO .
9519169 7/1995 WIPO .
9618738 6/1996 WIPO .

OTHER PUBLICATIONS

Sambrook et al., Molecular Cloning, A Lab. Manual, 2nd Ed., 16.2–16.30, 17.2–17.28, Cold Spring Harbor Lab. Press. 1989.

Hillier et al., "yp07h01.r1 Homo sapiens cDNA clone 186769 5' similar to contains [sic] TAR1 repetitive element," *EST–STS Database*, Accession No. H51921, Sep. 18, 1995.

Castellanos and Mazon, "Identification of Phosphotyrosine in Yeast Proteins and of a Protein Tyrosine Kinase Associated with the Plasma Membrane," *J. Biol. Chem.* 260(14):8240–8242 (1985).

Maness, "Nonreceptor Protein Tyrosine Kinases Associated with Neuronal Development," *Dev. Neurosci.* 14:257–270 (1992).

Seedorf et al., "TKA–1, a novel type of cellular tyrosine kinase binding protein, selectively activates the platelet–derived growth factor receptor signaling potential," *EMBL Database Entry HSTKA1MR*, Accession No. Z50150, XP002023872 (Apr. 1, 1996).

Weinmann et al., "Characterization of a Protein Cofactor That Mediates Protein Kinase A Regulation of the Renal Brush Border Membrane $Na^+$—$H^+$ Exchanger," *Journal of Clinical Investigation* 95:2143–2149 (1995).

Margolis et al., "EGF Induces Tyrosine Phosphorylation of Phospholipase C–II: A Potential Mechanism for EGF Receptor Signaling," *Cell* 57:1101–1107 (1989).

Mayer et al., "A Novel viral oncogene with structural similarity to phospholipase C," *Nature* 332:272–275 (Mar. 1988).

McKnight, "Functional Relationships between Transcriptional Control Signals of the Thymidine Kinase Gene of Herpes Simplex Virus," *Cell* 31:355–365 (1982).

Miller, "Human gene therapy comes of age," *Nature* 357:455–460 (1992).

Miller et al., "Generation of Helper–Free Amphotropic Retroviruses That Transduce a Dominant–Acting, Metotrexate–Resistant Dihydrofolate Reductase Gene," *Molecular Cell Biology* 5:431–437 (1985).

Mulligan, "The Basic Science of Gene Therapy," *Science* 260:926–932 (1993).

Nelson et al., "Detection of Acridinium Esters by Chemiluminescence," *Nonisotopic DNA Probe Techniques* ed. L.J. Kricka (San Diego:Academic Press, Inc. pp. 275–310 (1992).

Nishibe et al., "Increase of the Catalytic Activity of Phospholipase C–γ1 by Tyrosine Phosphorylation," *Science* 250:1253–1256 (1990).

Pawson and Schlessinger, "SH2 and SH3 domains," *Current Biology* 3(7):434–441 (1993).

Pawson and Gish, "SH2 and SH3 Domains: From Structure to Function," *Cell* 71:359–362 (1992).

Ponting and Phillips, "DHR domains in syntrophins, neuronal NO synthases and other intracellular proteins," *TIBS* 20:102–103 (1995).

Posada and Cooper, "Molecular Signal Integration. Interplay Between Serine, threonine and Tyrosine Phosphorylation," *Mol. Biol. of the Cell* 3:583–592 (1992).

Pursel et al., "Genetic Engineering of Livestock," *Science* 244:1281–1288 (1989).

Ridley and Hall, "The Small GTP–Binding Protein rho Regulates the Assembly of Focal Adhesions and Actin Stress Fibers in Response to Growth Factors," *Cell* 70:389–399 (1992).

Ridley et al., "The Small GTP–Binding Protein rac Regulates Growth Factor–Induced Membrane Ruffling," *Cell* 70:401–410 (1992).

(List continued on next page.)

*Primary Examiner*—Sally P. Teng
*Attorney, Agent, or Firm*—Lyon & Lyon LLP

[57] ABSTRACT

The present invention relates to TKA-1 polypeptides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for TKA-1 related diseases or conditions characterized by an abnormal interaction between a TKA-1 polypeptide and a TKA-1 binding partner.

9 Claims, 7 Drawing Sheets

OTHER PUBLICATIONS

Ronnstrand et al., "Characterization of Two Monoclonal Antibodies Reactive with the External Domain of the Platelet–derived Growth Factor Receptor," *J. Biol. Chem.* 263(21):10429–10425.

Sadowski et al., A Noncatalytic Domain Conserved among Cytoplasmic Protein–Tyrosine Kinases Modifies the Kinase Function and Transforming Activity of Fujinami Sarcoma Virus P130$^{gag-fps}$, *Mol. and Cell. Biol.* 6(12):4396–4408 (1986).

Schlessinger and Ullrich, "Growth Factor Signalling by Receptor Tyrosine Kinases," *Neuron* 9:383–391 (1992).

Schlessinger, "Signal transduction by allosteric receptor oligomerization,"*Trends Biochem. Sci.* 13:443–447 (1988).

Seedorf et al., "Analysis of Platelet–derived Growth Factor Receptor Domain Function Using a Novel Chimeric Receptor Approach," *J. Biol. Chem.* 266:12424–12431 (1991).

Seedorf et al., "Differential Effects of Carboxy–Terminal Sequence Deletions on Platelet–Derived Growth Factor Receptor Signaling Activities and Interactions with Cellular Substrates," *Molecular Cell Biology* 12:4347–4356 (1992).

Silver et al., "Amino terminus of the yeast GAL4 gene product is sufficient for nuclear localization," *Proc. Natl. Acad. Sci. USA* 81:5951–5955 (1984).

Snyder, "No endothelial NO," *Nature* 377:196–197 (1995).

Ullrich and Schlessinger, "Signal Transduction by Receptors with Tyrosine Kinase Activity," *Cell* 61:203–212 (1990).

van der Geer and Pawson, "The PTB domain: a new protein module implicated in signal transduction," *TIBS* 20:277–280 (1995).

Weinman et al., "Camp–mediated Inhibition of the Renal Brush Border membrane $Na^{+}$–$H^{+0}$ Exchanger Requires a Dissociable Phosphoprotein Cofactor," *Jrnl Clinical Investigation* 92:1781–1786 (1993).

Weinman et al., "Characterization of a Protein Cofactor That Mediates Protein Kinase A Regulation of the Renal Brush Border Membrane $Na^{+}$–$H^{+}$ Exchange," *Jrnl Clinical Investigation* 95:2143–2149 (1995).

Yang et al., "In Vivo and In Vitro Gene Transfer to Mammalian Somatic Cells by Particle Bombardment," *Proc. Natl. Acad. Sci. USA* 87:9568–9572 (1990).

Yarden and Ullrich, "Growth factor receptor tyrosine kinase," *Ann. Rev. Biochem.* 57:443–478 (1988).

Gottesman, "Bacterial Regulation: Global Regulatory Networks," *Ann. Rev. Genet.* 18:415–441 (1984).

Hamer and Walling, "Regulation In Vivo of a Cloned Mammalian Gene: Cadmium Induces the Transcription of a Mouse Metallothionein Gene in SV40 Vectors," *J. of Molecular and Applied Genetics* 1:273–288 (1982).

Hammer et al., "Spontaneous Inflammatory Disease in Transgenic Rats Expressing HLA–B27 and Human $\beta_2$m: An Animal Model of HLA–B27–Associated Human Disorders," *Cell* 63:1099–1112 (1990).

Hardie, "Roles of Protein Kinases and Phosphatases in Signal Transduction," *Symp. Soc. Exp. Bio.* 44:241–255 (1990).

Heinemann and Hahn, "Circular permutations of protein sequence: not so rare" *TIBS* 20:349–350 (1995).

Herbst et al., "Substrate Phosphorylation Specificity of the Human c–kit Receptor Tyrosine Kinase," *J. of Biol. Chem.* 266(30):19908–19916 (1991).

Honegger et al., "Evidence that autophosphorylation of solubilized receptors for epidermal growth factor is mediated by intermolecular cross–phosphorylation," *Proc. Natl. Acad. Sci. USA* 86:925–929 (1989).

Houdebine and Chourrout, "Transgenesis in Fish," *Experientia* 47:891–897 (1991).

Huang et al., "Hypertension in mice lacking the gene for endothelial nitric oxide synthase," *Nature* 377:239–242 (1995).

Johnston and Hopper, "Isolation of the yeast regulatory gene GAL4 and analysis of its dosage effects on the galactose/melibiose regulon," *Proc. Natl. Acad. Sci. USA* 79:6971–6975 (1982).

Joyner et al., "Production of a mutation in mouse En–2 gene by homologous recombination in embryonic stem cells," *Nature* 338:153–156 (1989).

Kim et al., "PDGF Stimulation of Inositol Phospholipid Hydrolysis Requires PLC–Vγ1 Phosphorylation on Tyrosine Residues 783 and 1254, " *Cell* 65:435–441 (1991).

Klingensmith et al., "The Drosophila segment polarity gene dishevelled encodes a novel protein required for response to the wingless signal, " *Genes & Development* 8:118–130 (1994).

Koch et al., "SH2 and SH3 Domains: Elements That Control Interactions of Cytoplasmic Signaling Proteins," *Science* 252:668–674 (1991).

Koonin et al., "dlg–R proteins: modified guanylate kinases," *Nature Genetics* 2:256–257 (1992).

Kornau et al., "Domain Interactions Between NMDA Receptor Subunits and the Postsynaptic Density Protein PSD–95," *Science* 269:1737–1740 (1995).

Kris et al., "Antibodies against a Synthetic Peptide as a Probe for the Kinase Activity of the Avian EGF Receptor and v–erbB Protein," *Cell* 40:619–625 (1985).

Lee et al., "HER2 cytoplasmic domain generates normal mitogenic and transforming signals in a chimeric receptor," *EMBO J.* 8:167–173 (1989).

Macgregor et al., "Direct cloning of leucine zipper proteins: Jun binds cooperatively to the CRE with CRE–BP1," *Oncogene* 5:451–458 (1990).

Maekawa, Kazuhiko et al., "Molecuar cloning of a novel protein–tyrosine phosphatase containing a membrane–binding domain and GLGF repeats," *FEBS* 337:200–206 (1994).

Margolis et al., "Effect of Phospholipase C–γ Overexpression on PDGF–Induced Second Messengers and Mitogenesis," *Science* 248:607–610 (1990).

Aaronson, "Growth Factors and Cancer," *Science* 254:1146–1153 (1991).

Abe et al., "Molecular Characterization of a Novel Metabotropic Glutamate Receptor mGluR5 Coupled to Inositol Pohosphate/$Ca^{2+}$ Signal," *J. Biol. Chem.* 19:13361–13368 (1992).

Benoist and Chambon, "In vivo sequence requirements of the SV40 early promoter region," *Nature* 290:304–310 (1981).

Blaike et al., "A Region in the Shc Distinct from the SH2 Domain Can bind Tyroxine–phosphorylated Growth Factor Receptors," *J. Biol. Chem.* 269:32031–32043 (1994).

Bosenberg et al., "The Cytoplasmic Carboxy–Terminal Amino Acid Specifies Cleavage of Membrane TGFα into Soluble Growth Factor," *Cell* 71:1157–1165 (1992).

Brinster et al., "Factors Affecting the Efficiency of Introducing Foreign DNA into Mice by Microinjecting Eggs," *Proc. Natl. Acad. Sci. USA* 82:4438–4442 (1985).

Bühring et al., "The Product of the Proto–oncogene c–kit ($P145_{c-kit}$) is a Human Bone Marrow Surface Antigen of Hemopoietic Precursor Cells which is Expressed on a Subset of Acute Non–lymphoblastic Leukemic Cells," *Leukemia* 5(10):854–860 (1991).

Capecchi, "Altering the Genome by Homologous Recombination," *Science*244:1288–1292 (1989).

Chen and Okayama, "High–Efficiency Transformation of Mammalian Cells by Plasmid DNA," *Mol. and Cell. Biol.* 7(8):2745–2752 (1987).

Curiel et al., "Gene Transfer to Respiratory Epithelial Cells via the Receptor–mediated Endocytosis Pathway," *Am. J. Respir. Cell. Mol. Biol.* 6:247–252 (1992).

Felgner et al., "Lipofection: A Highly Efficient, Lipid–mediated DNA–transfection Procedure," *Proc. Natl. Acad. Sci. USA* 84:7413–7417 (1987).

Felgner and Ringold, "Cationic liposome–mediated transfection," *Nature* 337:387–388 (1989).

Fendly et al., "Characterization of Murine Monoclonal Antibodies Reactive to Either the Human or Epidermal Growth Factor Receptor or HER2/neu Gene Product" *Cancer Research* 50:1150–1558 (1990).

Gorman et al., "The Human Cytomegalovirus Major Immediate Early Promoter Can Be trans–Activated by Adenovirus Early Proteins," *Virology* 171:377–385 (1989).

```
    GCC GCC GCT GAA GCC ACC GCC GGG TGC CCA GCG CCG CCG CCG CCC CCG AGC
                  9          18          27          36          45

                                                        Met Ala Ala Pro
TCC CCC GCG CCC CTG CCC GCG GGC GGC CGG TGG GCA GCG GGC GCC ATG GCC GCG CCG
         60          69          78          87          96         105

Glu Pro Leu Arg Pro Arg Leu Cys Arg Leu Val Arg Gly Glu Gln Gly Tyr Gly Phe
GAG CCG CTG CGG CCG CGC CTG TGC CGC TTG GTG CGC GGA GAG CAG GGC TAC GGC TTC
        117         126         135         144         153         162

His Leu His Gly Glu Lys Gly Arg Arg Gly Gln Phe Ile Arg Arg Val Glu Pro Gly
CAC CTG CAC GGC GAG AAG GGC CGC CGC GCG CAG TTC ATC CGG CGC GTG GAA CCC GGT
        174         183         192         201         210         219

Ser Pro Ala Glu Ala Ala Ala Leu Ala Gly Asp Arg Leu Val Glu Val Asn Gly Val
TCC CCC GCC GAG GCC GCC GCG CTG GCT GGG GAC CGC CTG GTC GAG GTC AAC GGC GTC
        231         240         249         258         267         276

Asn Val Glu Gly Glu Thr His His Gln Val Val Gln Arg Ile Lys Ala Val Glu Gly
AAC GTG GAG GGC GAG ACG CAC CAC CAG GTG GTG CAA AGG ATC AAC GCT GTG GAG GGG

        288         297         306         315         324         333
```

FIG. 1A

```
Gln Thr Arg Leu Leu Val Val Asp Gln Glu Thr Asp Glu Glu Leu Arg Arg Arg Gln
CAG ACT CGG CTG CTG GTG GTG GAC CAG GAG ACA GAT GAG GAG CTC CGC CGG CGG CAG
        345         354         363         372         381         390

Leu Thr Cys Thr Glu Glu Met Ala Gln Arg Gly Leu Pro Pro Ala His Asp Pro Trp
CTG ACC TGT ACC GAG GAG ATG GCC CAG CGA GGG CTC CCA CCC GCC CAC GAC CCC TGG
        402         411         420         429         438         447

Glu Pro Lys Pro Asp Trp Ala His Thr Gly Ser His Ser Ser Glu Ala Gly Lys Lys
GAG CCG AAG CCA GAC TGG GCA CAC ACC GGC AGC CAC AGC TCC GAA GCT GGC AAG AAG
        459         468         477         486         495         504

Asp Val Ser Gly Pro Leu Arg Glu Leu Arg Pro Arg Leu Cys His Leu Arg Lys Gly
GAT GTC AGT GGG CCC CTG AGG GAG CTG CGC CCT CGG CTC TGC CAC CTG CGA AAG GGA
        516         525         534         543         552         561

Pro Gln Gly Tyr Gly Phe Asn Leu His Ser Asp Lys Ser Arg Pro Gly Gln Tyr Ile
CCT CAG GGC TAT GGG TTC AAC CTG CAT AGT GAC AAG TCC CGG CCC GGC CAG TAC ATC
        573         582         591         600         609         618

Arg Ser Val Asp Pro Gly Ser Pro Ala Ala Arg Ser Gly Leu Arg Ala Gln Asp Arg
CGC TCT GTG GAC CCG GGC TCA CCT GCC GCC CGC TCT GGC CTC CGC GCC CAG GAC CGG
        630         639         648         657         666         675
```

FIG. 1B

```
Leu Ile Glu Val Asn Gly Gln Asn Val Glu Gly Leu Arg His Ala Glu Val Val Ala
CTC ATT GAG GTG AAC GGG CAG AAT GTG GAG GGA CTG CGC CAT GCT GAG GTG GTG GCC
        687         696         705         714         723         732

Ser Ile Lys Ala Arg Glu Asp Glu Ala Arg Leu Leu Val Val Asp Pro Glu Thr Asp
AGC ATC AAG GCA CGG GAG GAC GAG GCC CGG CTG CTG GTC GTG GAC CCC GAG ACA GAT
        744         753         762         771         780         789

Glu His Phe Lys Arg Leu Arg Val Thr Pro Thr Glu Glu His Val Glu Gly Pro Leu
GAA CAC TTC AAG CGG CTT CGG GTC ACA CCC ACC GAG GAG CAC GTG GAA GGT CCT CTG
        801         810         819         828         837         846

Pro Ser Pro Val Thr Asn Gly Thr Ser Pro Ala Gln Leu Asn Gly Gly Ser Ala Cys
CCG TCA CCC GTC ACC AAT GGA ACC AGC CCT GCC CAG CTC AAT GGT GGC TCT GCG TGC
        858         867         876         885         894         903

Ser Ser Arg Ser Asp Leu Pro Gly Ser Asp Lys Asp Thr Glu Asp Gly Ser Ala Trp
TCA TCC CGA AGT GAC CTG CCT GGT TCC GAC AAG GAC ACT GAG GAT GGC AGT GCC TGG
        915         924         933         942         951         960

Lys Gln Asp Pro Phe Gln Glu Ser Gly Leu His Leu Ser Pro Thr Ala Ala Glu Ala
AAG CAA GAT CCC TTC CAG GAG AGC GGC CTC CAC CTG AGC CCC ACG GCG GCC GAG GCA
        972         981         990         999        1008        1017

Arg Arg Arg Leu Glu Pro Cys Glu Ser Thr Ser Ala Arg His Arg Trp Thr Gly Thr
AGG AGA AGG CTC GAG CCA TGC GAG TCA ACA AGC GCG CGC CAC AGA TGG ACT GGA ACA
       1029        1038        1047        1056        1065        1074
```

FIG. 1C

```
Gly Ser Val Lys Ser Ser Ala Thr Ser Glu Pro Leu Pro Ala Cys Leu Gly Thr Leu
GGA AGC GTG AAA TCT TCA GCA ACT TCT GAG CCC CTT CCT GCC TGT CTC GGG ACC CTG
        1086        1095        1104        1113        1122        1131

Gly Pro Leu Pro His Gly Pro Trp Ala Ser Ala Cys Pro Glu Leu Pro Gln Pro Gln
GGA CCC CTC CCG CAC GGA CCT TGG GCC TCA GCC TGC CCC GAG CTC CCC CAG CCT CAG
        1143        1152        1161        1170        1179        1188

Trp Thr Gly Gly Trp Ser Cys His Cys Pro Glu Ile Ser Pro Ser Pro Gly Glu Pro
TGG ACT GGA GGG TGG TCC TGC CAT TGC CCA GAA ATC AGC CCC AGC CCC GGT GAG CCC
        1200        1209        1218        1227        1236        1245

Pro Ser Cys Pro Cys Pro Pro Gly Thr Gly Gly Leu Trp Gln Gln Asp Arg Gly Arg
CCA TCC TGC CCC TGC CCA CCA GGT ACT GGG GGC CTG TGG CAG CAA GAT AGG GGG AGA
        1257        1266        1275        1284        1293        1302

Glu Thr Gln Arg Cys Glu Arg Glu Ser Glu Thr Glu Thr Glu Arg Glu Arg Glu Arg
GAG ACC CAG AGA TGT GAG AGA GAG TCA GAG ACA GAG ACA GAG AGA GAG AGA GAG AGA
        1314        1323        1332        1341        1350        1359

His Arg Glu Arg Gln Arg Glu Ser Glu Arg Ala Arg Gly Ser Arg Gly Ala Arg Ala
CAC AGA GAG AGA CAG AGA GAG AGC GAG CGA GCG CGC GGC AGC CGC GGG GCG AGG GCC
        1371        1380        1389        1398        1407        1416
```

FIG. 1D

```
Phe Ala Ala Leu Pro Gly Pro Ala Asp TER
TTT GCT GCT CTG CCG GGG CCT GCT GAC TGA AAG GAA TTT GTG TTT TTG CTT TTT TTC
        1428        1437        1446        1455        1464        1473

CAA AAA GAT CTC CAG CTC CAC ACA TGT TTC CAC TTA ATA CCA GAG ACC CCC CCC TTC
        1485        1494        1503        1512        1521        1530

CCC TCC CCC TTC CCC TCC CCC TTG GGA CGC GCT CTA AAT AAT TGC AAT AAA ACA AAC
        1542        1551        1560        1569        1578        1587

CTT TCT CTG CAA AAA AAA AAA AAA AAA AAA AAA AAA AAA AAA AAA AAA AAA A
        1599        1608        1617        1626        1635
```

DIAGNOSIS AND TREATMENT OF TKA-1 RELATED DISORDERS

RELATED APPLICATIONS

The present application is a continuation-in-part application of U.S. application Ser. No. 08/666,067, filed Jun. 14, 1996, and is a continuation-in-part application of U.S. Pat. application Ser. No. 08/665,037 filed Jun. 13, 1996, which claims the benefit of U.S. Provisional Application No. 60/005,423, filed Oct. 13, 1995 and U.S. Provisional Application No. 60/005,167, filed Oct. 13, 1995, all of which are incorporated herein by reference in their entirety, including any drawings.

INTRODUCTION

The present invention relates to the novel protein termed tyrosine kinase associated protein one ("TKA-1"), nucleotide sequences encoding TKA-1, as well as various products and methods useful for the diagnosis and treatment of various TKA-1 related diseases and conditions.

BACKGROUND OF THE INVENTION

The following description of the background of the invention is provided to aid in understanding the invention, but is not admitted to describe or constitute prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of tyrosine residues on proteins. The phosphorylation state of a protein is modified through the reciprocal actions of tyrosine kinases (TKs) and tyrosine phosphatases (TPs).

Receptor tyrosine kinases (RTKs) belong to a family of transmembrane proteins and have been implicated in cellular signaling pathways. The predominant biological activity of some RTKs is the stimulation of cell growth and proliferation, while other RTKs are involved in arresting growth and promoting differentiation. In some instances, a single tyrosine kinase can inhibit or stimulate, cell proliferation depending on the cellular environment in which it is expressed. Schlessinger and Ullrich, *Neuron,* 9(3):383–391, 1992. The platelet derived growth factor receptor (PDGF-R) and the role of its ligand (i.e., PDGF) in cancer are described in International Patent Application WO 95/19169, published Jul. 20, 1995, incorporated herein by reference in its entirety including any drawings.

RTKs are composed of at least three domains: an extracellular ligand binding domain, a transmembrane domain and a cytoplasmic catalytic domain that can phosphorylate tyrosine residues. Yarden and Ullrich, *Ann. Rev. Biochem.* 57:443–478, 1988. Ligand binding to membrane-bound receptors induces the formation of receptor dimmers and allosteric changes that activate the intracellular kinase domains and result in the self-phosphorylation (autophosphorylation and/or transphosphorylation) of the receptor on tyrosine residues. Their intrinsic tyrosine kinase is activated upon ligand binding, thereby initiating a complex signal transduction pathway that begins with receptor autophosphorylation and culminates in the tyrosine phosphorylation of a variety of cellular substrates and ultimately in the initiation of nuclear events necessary for the overall cell response. Schlessinger and Ullrich, *Neuron* 9:383–391, 1992. Individual phosphotyrosine residues of the cytoplasmic domains of receptors may serve as specific binding sites that interact with a host of cytoplasmic signaling molecules, thereby activating various signal transduction pathways, Ullrich and Schlessinger, *Cell* 61:203–212, 1990.

The intracellular, cytoplasmic, non-receptor protein tyrosine kinases do not contain a hydrophobic transmembrane domain or an extracellular domain and share non-catalytic domains in addition to sharing their catalytic kinase domains. Such non-catalytic domains include the SH2 domains (SRC homology domain 2; Sadowski et al., *Mol. Cell. Biol.* 6:4396–4408; Koch et al., *Science* 252:668–674, 1991) SH3 domains (SRC homology domain 3; Mayer et al., *Nature* 332:269–272, 1988) and PI domains (also called PTB domains Blaike, et al., *JBC 269:32031–32034, 1994;* VanderGeer and Pawson *TIBS* 20: 277–280, 1995). The non-catalytic domains are thought to be important in the regulation of protein-protein interactions during signal transduction. Pawson and Gish, *Cell* 71:359–362, 1992.

A central feature of signal transduction (for reviews, see Posada and Cooper, *Mol. Biol. Cell* 3:583–392, 1992; Hardie, *Symp. Soc. Exp. Biol.* 44:241–255, 1990), is the reversible phosphorylation of certain proteins. Receptor phosphorylation stimulates a physical association of the activated receptor with target molecules. Some of the target molecules such as phospholipase Cγ are in turn phosphorylated and activated. Margolis et al., *Cell* 57:1101–1107, 1989; Margolis et al., *Science* 248:607–610, 1990; Nishibe et al., *Science* 250:1253–1255, 1990; and Kim et al., *Cell* 65:435–411, 1991. Such phosphorylation transmits a signal to the cytoplasm. Other target molecules are not phosphorylated, but assist in signal transmission by acting as adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras. Pawson and Schlessinger, *Current Biol.* 13:434, 1993.

Receptor phosphorylation is essential for binding and phosphorylation of cytoplasmic target proteins that contain SH2 domains, such as phospholipase Cγ (PLCγ), $p21^{ras}$ GTPase-activating protein (GAP), phosphatidylinositol (PI) 3'-kinase (PI3K), $p60^{arc}$ and related tyrosine kinases, growth factor receptor-bound protein 2 (GRB-2), vav, SHC, CRK, NCK, and PTP1D, (also called SH-PTP2 or syp) and for proteins that contain PI domains, such as SHC. High affinity binding of these signal-transducing factors is strictly dependent on SH2 domains and tyrosine-phosphorylated, short sequence motifs within different domains of the receptor tyrosine kinase (Koch, C. A. et al., (1991), *Science,* 252, 668–674).

The secondary signal transducer molecules generated by activated receptors result in a signal cascade that regulates cell functions such as cell division or differentiation. Reviews describing intracellular signal transduction include Aaronson, *Science,* 254:1146–1153, 1991; Schlessinger, *Trends Biochem. Sci.,* 13:443–447, 1988; and Ullrich and Schlessinger, *Cell,* 61:203–212, 1990. However, the search for receptor-specific signal transducers and regulators which (in addition to generally employed SH2 domain substrate proteins) define ligand- and cell type-characteristic effects has so far had only limited success.

SUMMARY OF THE INVENTION

The present invention relates to TKA-1 polypeptides, nucleic acids encoding such polypeptides, cells containing such nucleic acids, antibodies to such polypeptides, assays utilizing such polypeptides, and methods relating to all of the foregoing. The present invention is based in part upon the isolation and characterization of a new protein which we have designated TKA-1.

A cDNA clone encoding a novel type of tyrosine kinase-associated protein, designated TKA-1, was isolated from a λgt11 library. The TKA-1 cDNA encodes a protein of 47 kD, which specifically interacts with C-terminal sequences of the PDGF-R in a ligand-independent fashion without becoming tyrosine-phosphorylated itself. In vitro association experiments indicate that TKA-1, which is widely expressed in normal tissues and tumor cells, interacts tightly and specifically with the PDGF-R in spite of the absence of SH2 or PI domains. TKA-1 binding to structural determinants within the receptor's C-terminal tail results in ligand-independent receptor autophosphorylation, substrate phosphorylation, and activation of receptor-associated phosphatidylinositol (PI) 3'-kinase. TKA-1 overexpression enhances DNA synthesis in NIH3T3 fibroblasts and results in disintegration of actin filaments, similar to the transient effect caused by PDGF in nontransfected NIH 3T3 cells. The structural characteristics and functional properties described herein establish TKA-1 as a novel type of intracellular polypeptide involved in receptor-specific regulation of cellular signals.

Thus, in a first aspect the invention features an isolated, enriched, or purified nucleic acid encoding a TKA-1 polypeptide.

By "TKA-1 polypeptide" is meant an amino acid sequence substantially similar to the sequence shown in FIGS. 1A–C (SEQ ID NO:2), or fragments thereof. A sequence that is substantially similar will preferably have at least 90% identity (more preferably at least 95% and most preferably 99–100%) to the sequence of FIGS. 1A–C (SEQ ID NO:2).

By "identity" is meant a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements may have a lower degree of identity. Those skilled in the art will recognize that several computer programs are available for determining sequence identity.

By "isolated" in reference to nucleic acid is meant a polymer of 6 (preferably 21, more preferably 39, most preferably 75) or more nucleotides conjugated to each other, including DNA or RNA that is isolated from a natural source or that is synthesized. In certain embodiments of the invention longer nucleic acids are preferred, for example those of 300, 600, 900 or more nucleotides and/or those having at least 50%, 60%, 75%, 90%, 95% or 99% identity to the full length sequence shown in FIGS. 1A–C (SEQ ID NO:1). The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it and thus is meant to distinguish from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of Mycogen/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "a TKA-1 polypeptide" is meant 25 (preferably 30, more preferably 35, most preferably 40) or more contiguous amino acids set forth in the full length amino acid sequence of FIGS. 1A–C (SEQ ID NO:2), or a functional derivative thereof as described herein. In certain aspects, polypeptides of 100, 200, 300 or more amino acids are preferred. The TKA-1 polypeptide can be encoded by a full-length nucleic acid sequence or any portion of the full-length nucleic acid sequence, so long as a functional activity of the polypeptide is retained. Such functional activity can be, for example: (1) stimulation of ligand-independent receptor autophosphorylation, (2) substrate phosphorylation, (3) activation of receptor-associated phosphatidylinositol (PI) 3'-kinase, (4) enhanced DNA synthesis in NIH3T3 fibroblasts and (5) disintegration of actin filaments and (6) receptor dimerization.

In preferred embodiments the isolated nucleic acid comprises, consists essentially of, or consists of a nucleic acid sequence set forth in the full length nucleic acid sequence of FIGS. 1A–C (SEQ ID NO:1), a functional derivative thereof, or encodes at least 25, 30, 35, 40, 50, 100, 200, or 300 contiguous amino acids thereof; the TKA-1 polypeptide comprises, consists essentially of, or consists of at least 25, 30, 35, or 40 contiguous amino acids of a TKA-1 polypeptide. The nucleic acid may be isolated from a natural source by cDNA cloning or subtractive hybridization; the natural source may be mammalian (human) blood, semen, or tissue and the nucleic acid may be synthesized by the triester method or by using an automated DNA synthesizer. In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions.

By "conserved nucleic acid regions", are meant regions present on two or more nucleic acids encoding a TKA-1 polypeptide, to which a particular nucleic acid sequence can hybridize under lower stringency conditions. Examples of lower stringency conditions suitable for screening for nucleic acid encoding TKA-1 polypeptides are provided in Abe, et al. *J. Biol. Chem.,* 12:13361 (1992) (hereby incorporated by reference herein in its entirety, including any drawings). Preferably, conserved regions differ by no more than 5 out of 20 nucleotides.

By "unique nucleic acid region" is meant a sequence present in a full length nucleic acid coding for a TKA-1 polypeptide that is not present in a sequence coding for any other naturally occurring polypeptide. Such regions preferably comprise 30 or 45 contiguous nucleotides present in the full length nucleic acid encoding a TKA-1 polypeptide. In particular, a unique nucleic acid region is preferably of mammalian origin.

The invention also features a nucleic acid probe for the detection of a TKA-1 polypeptide or nucleic acid encoding a TKA-1 polypeptide in a sample. The nucleic acid probe contains nucleic acid that will hybridize to a sequence set forth in FIGS. 1A–C (SEQ ID NO:1) or a functional derivative thereof.

In preferred embodiments the nucleic acid probe hybridizes to nucleic acid encoding at least 12, 75, 90, 105, 120, 150, 200, 250, 300 or 350 contiguous amino acids of the full-length sequence set forth in FIGS. 1A–C (SEQ ID NO:2) or a functional derivative thereof. Various low or high stringency hybridization conditions may be used depending upon the specificity and selectivity desired. Under stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount TKA-1 RNA in a sample by contacting the sample with a nucleic acid probe under conditions such that hybridization occurs and detecting the presence or amount of the probe bound to TKA-1 RNA. The nucleic acid duplex formed between the probe and a nucleic acid sequence coding for a TKA-1 polypeptide may be used in the identification of the sequence of the nucleic acid detected (for example see, Nelson et al., in *Nonisotopic DNA Probe Techniques,* p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention also features recombinant nucleic acid, preferably in a cell or an organism. The recombinant nucleic acid may contain a sequence set forth in FIGS. 1A–C (SEQ ID NO:1) or a functional derivative thereof and a vector or a promoter effective to initiate transcription in a host cell. The recombinant nucleic acid can alternatively contain a transcriptional initiation region functional in a cell, a sequence complementary to an RNA sequence encoding a TKA-1 polypeptide and a transcriptional termination region functional in a cell.

In another aspect the invention features an isolated, enriched, or purified TKA-1 polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. In certain aspects longer polypeptides are preferred, such as those with 402, 407, 413, or 425 contiguous amino acids set forth in FIGS. 1A–C (SEQ ID NO:2). The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which man has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of Mycogen/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments the TKA-1 polypeptide contains at least 25, 30, 35, 40, 50, 100, 150, 200, 250, 300, or 350 contiguous amino acids of the full-length sequence set forth in FIGS. 1A–C (SEQ ID NO:2), or a functional derivative thereof.

In yet another aspect the invention features an antibody (e.g., a monoclonal or polyclonal antibody) having specific binding affinity to a TKA-1 polypeptide. The antibody contains a sequence of amino acids that is able to specifically bind to a TKA-1 polypeptide. By "specific binding affinity" is meant that the antibody binds to TKA-1 polypeptides with greater affinity than it binds to other polypeptides under specified conditions.

Antibodies having specific binding affinity to a TKA-1 polypeptide may be used in methods for detecting the presence and/or amount of a TKA-1 polypeptide in a sample by contacting the sample with the antibody under conditions such that an immunocomplex forms and detecting the presence and/or amount of the antibody conjugated to the TKA-1 polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a TKA-1 polypeptide. By "hybridoma" is meant an immortalized cell line which is capable of secreting an antibody, for example a TKA-1 antibody. In preferred embodiments the TKA-1 antibody comprises a sequence of amino acids that is able to specifically bind a TKA-1 polypeptide.

In another aspect, the invention describes a polypeptide comprising a recombinant TKA-1 polypeptide or a unique fragment thereof. By "unique fragment," is meant an amino acid sequence present in a full-length TKA-1 polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence.

By "recombinant TKA-1 polypeptide" is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In another aspect, the invention describes a recombinant cell or tissue containing a purified nucleic acid coding for a TKA-1 polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the TKA-1 polypeptide.

In another aspect, the invention features a TKA-1 polypeptide binding agent able to bind to a TKA-1 polypeptide. The binding agent is preferably a purified antibody which recognizes an epitope present on a TKA-1 polypeptide. Other binding agents include molecules which bind to the TKA-1 polypeptide and analogous molecules which bind to a TKA-1 polypeptide. Such binding agents may be identified by using assays that measure TKA-1 binding partner activity, such as those that measure PDGFR activity.

By "purified" in reference to an antibody is meant that the antibody is distinct from naturally occurring antibody. Preferably, the antibody is provided as a homogeneous preparation by standard techniques. Uses of antibodies to the cloned polypeptide include those to be used as therapeutics, or as diagnostic tools.

In another aspect, the invention features a method of disrupting or promoting receptor dimerization. The method involves providing a TKA-1 small molecule mimetic (i.e., an organic chemical that mimics the activity of TKA-1 to bind to and activate TKA-1 binding partners) to a TKA-1 binding partner complex. Alternatively, the method may involve providing the full length TKA-1 protein or a large fragment thereof (i.e., at least 80%, or preferably 90% sequence similarity or identity to the full length TKA-1 sequence) to a binding partner. Such a method will preferably aid in tissue regeneration.

In another aspect, the invention features methods of identifying TKA-1 like molecules that have at least one and preferably two or more GLGF or DHR motifs. Such motifs are described in further detail below and are defined and exemplified in Heinemann and Hahn, *TIBS,* 20:102–104, September 1995, incorporated herein by reference in its entirety including any drawings. Such molecules are believed to be important in receptor dimerization.

Thus, the invention features a method for screening for human cells containing a TKA-1 polypeptide or an equivalent sequence. The method involves is identifying the novel polypeptide in human cells using techniques that are routine and standard in the art, such as those described herein for identifying TKA-1 (e.g., cloning, Southern or Northern blot analysis, in situ hybridization, PCR amplification, etc.). Novel methods are also provided which utilize an entire chimera RTK, but otherwise are the same as the CORT techniques described in International Patent application WO 92/13001, published Aug. 6, 1992, incorporated herein by reference in its entirety, including any drawings.

The invention also features methods of screening mammalian (preferably human,) cells for binding partners of TKA-1 polypeptides and screening these and other organisms for TKA-1 or the corresponding binding partner. The present invention also features the purified, isolated or enriched versions of the peptides identified by the methods described above.

In another aspect, the invention provides an assay to identify agents capable of interfering with the interaction between TKA-1 and a TKA-1 binding partner or between a TKA-1 like molecule having one or two or more GLGF or DHR domains and a binding partner for such a TKA-1 like molecule. Such assays may be performed in vitro or in vivo and are described in detail in Examples 8–10 herein. Other such assays can be obtained by modifying existing assays. For example the growth assay described in Ser. No. 08/487,088, filed Jun. 7, 1995, now abandoned (incorporated herein by reference including any drawings) may be modified by using the 293 cells described in Example 3 herein.

In another aspect the invention provides isolated domains and deletion mutants (as well as sequences that hybridize to the full length TKA-1 sequence under stringent hybridization conditions and that encodes a TKA-1 protein) as well as the nucleic acids encoding the same. The isolated domains can be used in screening assays to find specific inhibitors and the three dimensional structure of the domains can be used in the rational design of inhibitors. In particular, the GLGF domain described herein (also referred to as the PDZ domain) appears to play an important role in many protein-protein signalling interactions, as shown in FIG. 2. This domain appears twice within the full-length TKA-1 sequence and spans amino acids 7–89 and 146–229 of the full length TKA-1 amino acid sequence set forth in FIGS. 1A–C (SEQ ID NO:2). The underlined regions of sheet FIGS. 1A–C reflect areas of internal homology that are longer than, and thus include, the GLGF domains. Another set of internally homologous domains is underlined at amino acids 346–360 and 361–376. The consensus recognition binding sequence for this domain is (S/T)XV, and the interaction region located at the c-terminus of PDGFR is SFL (L is a conservative substitution).

The summary of the invention described above is non-limiting and other features and advantages of the invention will be apparent from the following description of the preferred embodiments, and from the claims.

BRIEF DESCRIPTION OF THE DRAWINGS

Figure 1F:
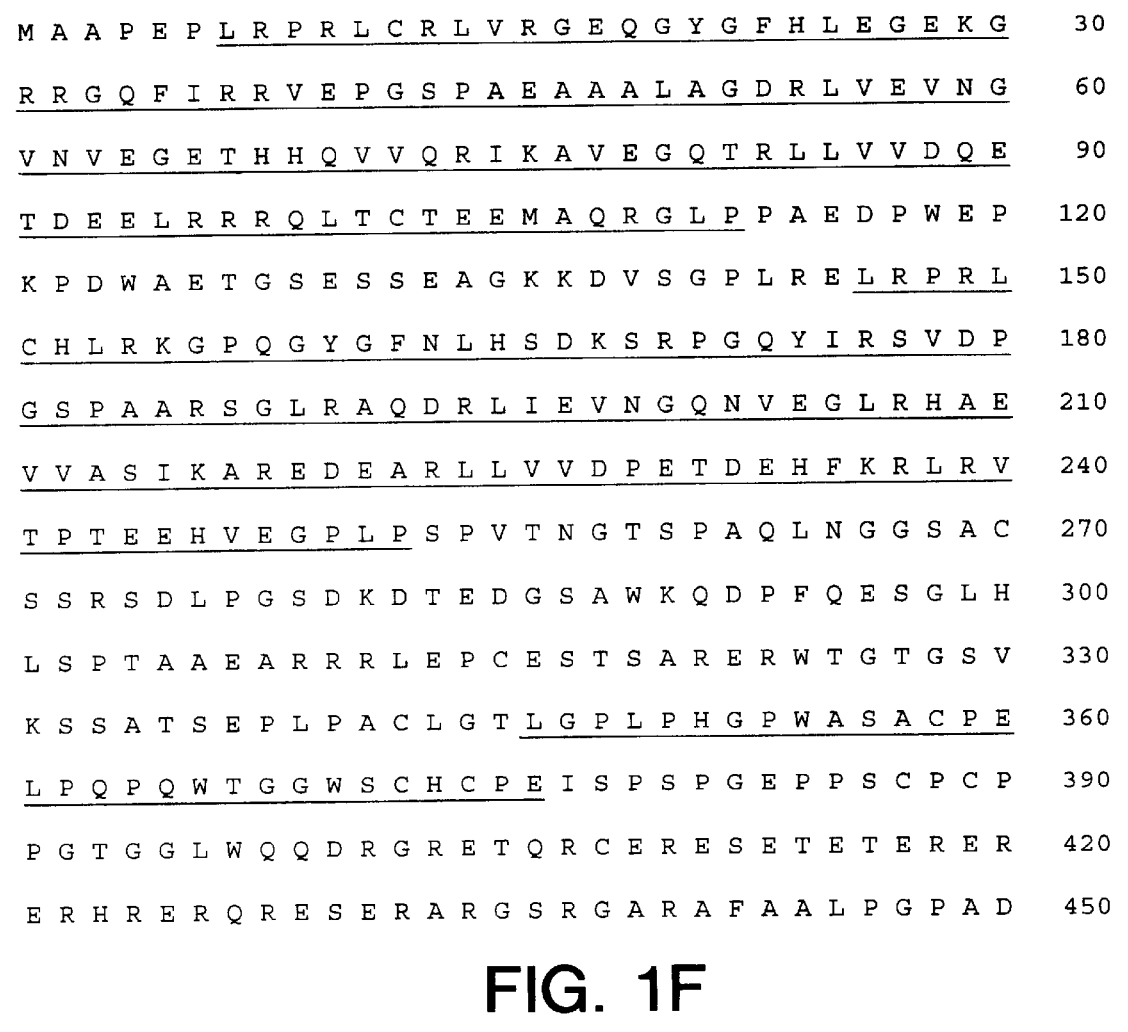

FIGS. 1A–C depict the full length nucleic acid sequence (SEQ ID NO:1) and amino acid sequence (SEQ ID NO:2) of TKA-1. The overlined regions of the amino acid sequence (SEQ ID NO:2) represent long and short internal repeats.

In FIG. 2, the term "NOS" refers to neuronal nitric oxide synthase; "PSD-95" (SAP90) refers to post-synaptic density protein; "HDLG" (SAP97) refers to large discs tumor suppressor; "KAP5" refers to PSD95-related; and "TKA-1" refers to tyrosine kinase binding protein.

DESCRIPTION OF THE PREFERRED EMBODIMENTS

Figure 2:
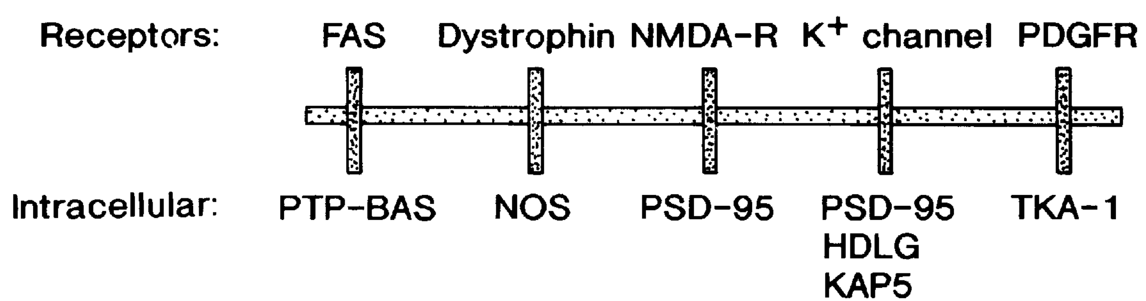
FIG. 2 depicts several GLGF domain interactions between various receptors and intracellular molecules.

The present invention relates to TKA-1 polypeptides, nucleic acids encoding such polypeptides, cells, tissues and animals containing such nucleic acids, antibodies to such polypeptides, assays utilizing such polypeptides, and methods relating to all of the foregoing.

I. Novel Cloning Methods and Signal Molecules Lacking known Interation Domains

We present here the cloning and characterization of cDNA sequences encoding TKA-1, an intracellular factor that selectively binds to PDGFα and β receptors and thereby activates their signaling capacity. Using an activated autophosphorylated receptor chimera consisting of the EGF-R binding and βPDGF-R signaling domains as a probe, one clone was identified in a human placenta λgt11 expression library that encoded a novel binding protein, designated TKA-1, in addition to clones representing mRNA copies for the p85 noncatalytic subunit of PI3K. Because the latter had previously been shown to exhibit very high affinity to the PDGF-R, TKA-1 binding, which occurred under the same experimental conditions during the screening process, appeared to be within a similar range.

Surprisingly, as revealed by cDNA sequencing, the encoded protein did not initially appear to contain an SH2 domain or any other sequence motif known to be involved in protein-protein interactions. Thus, TKA-1 represents a non-SH2 domain-containing factor involved in transmission and regulation of tyrosine kinase signals. Moreover, TKA-1 is not phosphorylated on tyrosines but appears to be constitutively phosphorylated on four Ser/Thr residues resulting in a 53kD form. Without wishing to be bound to any particular theory of the invention, the existence of two homologous 106 amino acid-long sequences suggests that one TKA-1 molecule may interact simultaneously with two PDGF-R molecules, mediating the generation of a receptor dimer. These homologous sequences have now been identified as GLGF or DHR motifs (see Heinemann and Hahn, *TIBS,* 20:102–104, September 1995, incorporated herein by reference in its entirety including any drawings).

Such motifs are recognized as important binding motifs and are believed to bind to the C-terminus of receptors through conserved terminal sequences. PDGF-R conforms to this consensus sequence. References describing these motifs and their functional importance include Weinman et al., *Jrnl Clinical Investigation* 95:2143–2149, 1995; Weinman et al., *Jrnl Clinical Investigation* 92:1781–1786, 1993; Koonin et al, *Nature Genetics* 2:256–257, 1992; Klingensmith et al., *Genes & Development* 8:118–130, 1994; Kazuhiko et al., *FEBS* 337:200–206, 1994; Kornau et al., *Science* 269:1737–1740, 1995; Snyder, *Nature* 377:196–197, 1995; Huang et al., *Nature* 377:239–242, 1995; Bosenberg et al., *Cell 71:1157–1165, 1992;* and Ponting and Phillips, *TIBS* 20:102–103, 1995, all of which are incorporated herein in their entirety including drawings.

II. PDGF-R Dimerization and Activation

Overexpression of TKA-1 induces biochemical and biological effects normally only induced by ligand-stimulated receptor dimerization and activation. These include receptor autophosphorylation, PI3K binding and activation, the promotion of thymidine incorporation in cellular DNA, and changes in cell morphology normally only observed upon exposure of fibroblasts to PDGF suggesting that TKA-1 may act as an alternative to ligand dependent PDGF-R activation. These effects on the morphology and physiology of cells appear to be caused upon interaction of TKA-1 with C-terminal sequences of the PDGF-R, a region that also contains phosphotyrosine binding sites for SH2 domain signal-transducing proteins such as PLCγ and PTP1D (Claesson-Welch, L. (1994), *J. Biol. Chem.* 269:32023–32026). Moreover, the 47 kD form of this unusual RTK signal regulator interacts, when associated with cell membranes, with several polypeptides in addition to the receptor.

Overexpression of TKA-1 is accompanied by the constitutive loss of actin filaments, analogous to that induced by exogenous PDGF treatment. Such PDGF-dependent decrease of stress fibers and the appearance of edge ruffles has been reported by several groups. Reports by Ridley, A. J. and Hall A., (1992), *Cell,* 70:389–399 and Ridley, A. J. et al., (1992), *Cell,* 70:401–410 showed that actin reorganization to form membrane ruffles is dependent on rac1 and the formation of stress fibers on rho, two small ras-related GTP-binding proteins. This would indicate that in NIH3T3 fibroblasts, both TKA-1 and PDGF activate rac1 and inactivate rho. In TKA-1-expressing cells, inactivation of rho appears to be constitutive, while in normal NIH3T3 fibroblasts the PDGF-induced effect is transient. Although this is a likely explanation, we cannot exclude the possibility that TKA-1 has a direct effect on actin reorganization. While TKA-1 activates the PDGF-R and PDGF-mediated effects to a lesser extent than PDGF, the two factors appear to act additively, suggesting either that TKA-1 and PDGF activate distinct PDGF-R fractions or that simultaneous interaction with extracellular and cytoplasmic receptor sequences results in a hyperactive state.

A potentially more complex role of TKA-1 in signal regulation is suggested by our Northern blot analysis, which revealed the existence of three transcripts of 1.4, 1.6, and 2.2 kb, of which the 1.6 kb form most likely corresponds to our cloned cDNA. The differential expression of these mRNAs in different tissues and even in the same cell type, as shown by the analysis of a panel of mammary carcinoma cell lines, further suggests functional significance for the physiology of the cell and possibly even direct relevance for the pathophysiological state of cancer cells.

In summary, our data show that TKA-1 acts like a PDGF-R-specific intracellular ligand, which upon binding activates tyrosine kinase activity and subsequent effects. Our data suggest the possibility that TKA-1 plays a role in cell survival in the absence of extracellular ligands or in cell locomotion. This is supported by immunofluorescence microscopy on TKA-1-overexpressing cell lines, which revealed intense localization at cell edges, consistent with signals necessary for cell movement, a process that appears to involve activated PI-3 kinase (Kundra, V. et al., (1994), *Nature,* 367:474–476). The signal-activating function of TKA-1 suggests novel regulatory mechanisms, which open new possibilities for crosstalk with other receptor and effector systems.

Various other features and aspects of the invention include: Nucleic Acid Encoding A TKA-1 Polypeptide; A Nucleic Acid Probe for the Detection of TKA-1; A Probe Based Method And Kit For Detecting TKA-1; DNA Constructs Comprising a TKA-1 Nucleic Acid Molecule and Cells Containing These Constructs; Purified TKA-1 Polypeptides; An Antibody Having Binding Affinity To A TKA-1 Polypeptide And A Hybridoma Containing the Antibody; An Antibody Based Method And Kit For Detecting TKA-1; Isolation of Compounds Which Interact With TKA-1; Transgenic Animals; and Gene Therapy. All of these aspects and features are explained in detail with respect to a protein termed PYK-2 in PCT publication WO 96/18738 (published Jun. 20, 1996), which is incorporated herein by reference in its entirety including any drawings. Those skilled in the art will readily appreciate that such description can be easily adapted to TKA-1 as well and is equally applicable to the present invention.

EXAMPLES

The examples below are non-limiting and are merely representative of various aspects and features of the present invention. The examples below demonstrate the isolation, and characterization of the novel tyrosine kinase associated protein, TKA-1.

Material and Methods Isolation and labelling of the EGF-PDGF-receptor chimera

A chimeric receptor consisting of the extracellular and transmembrane domains of the EGF receptor and the cytoplasmic domain of the PDGF-receptor (EP-R) was purified from 293 cells that were transiently transfected with a cytomegalovirus (CMV) promoter-driven EP-R expression plasmid by immunoprecipitation using protein A and monoclonal antibody (MAb) 108.1 (Honegger, A. M. et al., (1989), *Proc. Natl. Acad. Sci.* USA, 86, 925–929). The immune complex was washed three times with HNTG-buffer (20 mM HEPES, pH 7.5, 150 mM NaCl, 10% glycerol) containing 0.1% Triton X-100 and subsequently with kinase-buffer (20 mM HEPES, pH 7.5, 1 mM $MnCl_2$10% glycerol). Labelling of the receptor was carried out in 50 ml of kinase buffer containing 100 mCi $^{32}P_g$ATP at room temperature on a shaker for 40 minutes. Subsequently, cold ATP was added (2.5 ml of a 1 mM solution) and the incubation was continued for another 10 minutes. Unincorporated ATP was removed by washing three times with HNTG buffer. After the immune complex was disrupted by incubation in 0.2M glycine, pH 2.5, the protein A sepharose was removed by centrifugation and the supernatant neutralized with 1M Tris-HCl, pH 8.8.

Screening of λgt11 expression library

A λgt11 library constructed from human placenta mRNA (Clontech) was plated at a density of $5\times10^4$ plaques per 150 mm agar plate. A total of $5\times10^5$ plaques were initially screened. After incubation of the plates for 4 hours at 42° C., the plates were overlaid with isopropyl-b-D-thiogalactopyranoside (IPTG) impregnated filters, as described by Macgregor, P. F. et al., (1990), Oncogene, 5, 451–458. Incubation was continued overnight at 37° C. The filters were removed, washed several times with TBST buffer (10 mM Tris-HCl pH 8.0, 150 mM NaCl, 0.05% Triton X-100), and subsequently incubated in TBST containing 5% Carnation dry milk for 4 hours at 4° C. Then in vitro tyrosine-phosphorylated receptor was added (~$1\times10^6$ cpm/ml) and incubation continued overnight. The filters were washed 5 times at room temperature in phosphate-buffered saline containing 0.2% Triton X-100. Filters were dried and exposed to X-ray film at −80° C. Positive plaques were enriched by sequential screenings and the cDNA insert was sequenced after subcloning into Bluescript.

Expression vector construction and generation of stable cell transfectants

The chimeric receptor EP-R, EP-R deletion mutants, HER1-2, and EK-R, are described elsewhere (Seedorf, K. et al., (1991), *J. Biol. Chem.,* 266, 12424–12431; Seedorf, K. et al., (1992), *Mol. Cell. Biol.,* 12, 4347–4356; Lee, J et al., (1989), *EMBO J.,* 8, 167–173; Herbst, R. et al., (1991), *J. Biol. Chem.,* 266,19908–19916). The TKA-1 cDNA was cloned via EcoRI into a CMV promoter-driven expression vector for transient expression in 293 cells. For the generation of stably expressing NIH3T3 cells, TKA-1 cDNA was cloned via the same restriction site into pLEN. Ecotrophic recombinant retrovirus stocks were prepared from the helper virus-free producer line GP+E-86 (Markovitz et al., 1988). Low-titer amphotrophic virus, which was generated by transient transfection of retrovirus expression plasmids into the helper virus-free packaging cell line PA 317 (Miller, A. D. et al., (1985), *Mol. Cell. Biol.,* 5, 431–437), was used to infect GP+E-86 secondary packaging cells, followed by selection of GP+E-86 producer cells in G418 (1 mg/ml). The virus titer was determined by infection of NIH3T3 cells with serial dilutions and determination of G418-resistant colonies. The titers were between 2 and $5\times10^5$. For retrovirus-mediated gene transfer, subconfluent NIH3T3 cells ($10^5$ cells per 6-cm dish) were incubated with supernatants of GP+E-86 producer cells in the presence of Polybrene (4 mg/ml; Aldrich) overnight, followed by selection with G418. Stable expression of TKA-1 was determined by Western blot analysis using TKA-1-specific antibodies.

Transfections and immunoprecipitation

Polyclonal antibodies against TKA-1 were produced by immunizing rabbits with a glutathione-S-transferase fusion protein containing the entire coding region of TKA-1 expressed in *E. coli.* The EGF-R and EP-R chimera were precipitated with MAb 108.1. For detection in Western blots, a polyclonal antisera directed against the extracellular domain of the EGF-R was used. The PDGF-β-R was precipitated using antisera B2 (Ronnstrand et al., *JBC* 263(21): 10429–10425, 1988) and monoclonal antibody 28D4C10 (kindly provided by H. J. Bühring et al, *Leukemia* 5 (10): 854–860, 1991).

High efficiency transfection of human kidney fibroblasts (293 cells) was essentially performed as described by Chen, C. and Okayama, H. (1987), *Mol. Cell. Biol.,* 7, 2745–2752 and Gorman, C. M. et al., (1989), *Virology,* 171, 377–385. For labeling, medium was replaced by methionine free DMEM containing 0.5% FCS and 60 mCi [$^{35}$S] methionine/ml. Cells were treated with ligand and lysed as described by Kris, R. M. et al., (1985), *Cell,* 40, 619–625. Immunoprecipitates were separated on 7.5% PAA gels, transferred to nitrocellulose and incubated with a mouse monoclonal antibody directed against phosphotyrosine (5E2; Fendly, B. M. et al., (1990), *Cancer Res.,* 50, 1550–1558), TKA-1, and EGF-R, respectively. Protein bands were made visible using horseradish peroxidase-coupled goat anti-mouse and goat anti-rabbit antibodies and the ECL (Amersham) detection method.

Northern blot analysis

Poly $(A)^+$RNA was prepared from human tissue or tumor cell lines as described by Sambrook et al. (1989). For Northern analysis, 3 mg RNA were size-fractionated by electrophoresis in a 1.2% agarose-2.2M formaldehyde gel, transferred to a nitrocellulose membrane and backed at 80° C. for 2 hours. Following prehybridization, the blot was hybridized with a $^{32}$P-labelled TKA-1 probe. Hybridization was carried out overnight at 42° C. in the presence of 50% formamide, 5×SSC, 0.1% SDS, and 5×Denhardt's solution. The membrane was then washed in 0.1×SSC, 0.1% SDS at 42° C. and exposed to X-ray film at −80° C. for 48 hours using an intensifying screen.

Thymidine incorporation assay

Cells ($_{10}{}^5$ per well) were seeded into 24-well dishes pretreated with 0.2% gelatin. Cells were grown for 3 days in DMEM containing 10% FCS and then starved for 48 hours in 0.5% FCS. PDGF was added for 18 hours and subsequently [$^3$H] thymidine (0.5 mCi/well) for 4 hours. The cells were washed three times with PBS and incubated with ice cold 10% trichloroacetic acid (TCA) for 30 minutes. After washing twice with the same solution, the TCA precipitate was solubilized in 0.2M NaOH, 1% SDS, neutralized, and counted in a scintillation counter.

Actin reorganization

Cells were seeded on coverslips and incubated for 24 hours in DMEM, 10% FCS and subsequently for 24 hours in DMEM, 0.5% FCS. PDGF-BB was added at a concentration of 10 ng/ml for various times, washed three times with PBS, and fixed for 20 minutes at room temperature in 3% paraformaldehyde freshly prepared in PBS. After permeabilization with −20° C. acetone for 2 minutes, cells were stained with rhodamine-conjugated phalloidin (50 mg/ml in PBS, Sigma). After washing in PBS, coverslips were mounted in PBS/glycerol 1:1 and viewed in a Zeiss fluorescence microscope.

EXAMPLE 1 cDNA isolation and characterization

To identify novel polypeptides that bind with high affinity to RTKs and may be involved in regulation or transduction of cellular signals, we followed the CORT procedure but utilized, instead of a phosphorylated receptor fragment, an entire in vitro autophosphorylated receptor in form of the RTK chimera, EP-R, which consists of extracellular EGF binding and PDGF-β receptor cytoplasmic sequences (Seedorf, K. et al., (1991), *J. Biol. Chem.,* 266, 12424–12431), as a probe on a human placental λgt11 expression library. Screening of $3\times10^5$ plaques yielded 8 positive signals. The cDNA inserts of the recombinant λ phage were subcloned and partially sequenced. Seven of these proved to encode the noncatalytic subunit of PI3K, p85, which demonstrated that the experiment was successful. One clone with a cDNA insert of about 1600 bp encoded an apparently novel polypeptide, which was designated tyrosine kinase activator protein 1 (TKA-1). Protein sequence database searches yielded no match with known proteins.

To examine whether binding of the recombinant λgt11-encoded lacZ fusion protein could be reproduced in vitro, a glutathione S-transferase TKA-1 fusion protein was generated by cloning the partial TKA-1 cDNA into a pGEX bacterial expression vector. This purified glutathione S-transferase TKA-1 fusion protein was then shown to associate specifically with the immunoprecipitated EP-R chimera by immunoblot analysis using anti-glutathione S-transferase-specific antibodies.

Translation of the complete nucleotide sequence revealed an open reading frame of 450 amino acids FIGS. 1A–C (SEQ ID NO:2). To examine whether this cDNA represented a full-length clone, we screened a λZAP cDNA library prepared from SK-BR-3 mammary carcinoma cell mRNA with a $^{32}$P-labeled 5' clone 17 fragment. Several positives were isolated and analyzed by restriction and sequence analysis. None of these clones had an extended 5' end, and one was identical to clone 17, while the others were shorter.

TKA-1 has a translation initiation codon at position 97 (ATG), flanked by nucleotides matching Kozak's criteria for a translation initiation site (Kozak, M. (1991), *J. Biol. Chem.,* 266, 19867–19870), a stop codon (TGA) at position 1447, and a polyadenylation signal sequence (AATAAA) at position 1579–1585. Sequence comparison analysis using GenBank revealed that TKA-1 contains no src homology region 2 (SH2) or 3 (SH3) domains nor has the coding sequence any striking homology with other proteins. A stretch of 106 amino acids (aa 7–112) is duplicated within the sequence (aa 146–252) with 65% identity, and a second stretch of 15 amino acids (aa 346–360 and 361–376) with 47% identity. The calculated molecular mass of the protein encoded by the longest open reading frame beginning with a methionine codon was 49,346.

EXAMPLE 2

Northern blot analysis

To determine the expression of TKA-1 mRNA in various human tissues, Northern blot analysis was performed using a DNA probe corresponding to the first 1,032 nucleotides. 3 μg of poly$(A)^+$mRNA obtained from various human tissues (A) or mammary carcinoma cell lines (B) were separated on a 1.2% agarose-formaldehyde gel, transferred to nitrocellulose, and hybridized with a $^{32}$P-labeled, 1,031-nucleotide long TKA-1 cDNA fragment. Exposure time was 4 days at −70° C. with an intensifying screen.

Three hybridizing mRNA bands of 2.2, 1.6, and 1.4 kb were observed. The 1.6 and 1.4 kb mRNAs were found in all tissues analyzed, while the 2.2 kb mRNA was expressed in brain, liver, placenta, spleen, kidney, and duodenum, but not in muscle and stomach. Differential quantitative and qualitative expression of three TKA-1 mRNAs in several mammary carcinoma-derived cell lines suggest a functional significance. The fact that the largest mRNA expressed in SK-BR-3 cells was the 1.6 kb species supported our conclusion that our cDNA clone represented a full-length copy of this TKA-1 mRNA.

EXAMPLE 3

Expression of TKA-1 in 293

The complete TKA-1 cDNA was cloned into a CMV early promoter-driven expression vector for transient expression in 293 cells (ATCC# CRL 1573). After transfection and metabolic labeling, the cells were lysed or separated into cytosol and membrane fractions. TKA-1 was subsequently precipitated with a TKA-1-specific antiserum and analyzed by SDS-PAGE.

In particular, 293 cells transiently transfected with TKA-1 expression plasmid were biosynthetically labeled and lysed or fractionated into soluble and membrane-bound polypeptides. TKA-1 was subsequently immunoprecipitated using TKA-1-specific antisera from the soluble fraction, the membrane fraction, and from total cell lysates. In parallel, EP-R and TKA-1 expression plasmids were simultaneously transfected and EP-R immunoprecipitated from total cell lysates using MAb 108.1. In one lane, 293 cell lysates containing overexpressed TKA-1 were treated with MAb 108.1, while in another lane, TKA-1 was immunoprecipitated from nontransfected 293 cells. Polypeptides were separated on a 7.5% SDS-PAGE gel and exposed for 48 hours to X-ray film.

Precipitation of TKA-1 from [$^{35}$S]methionine-labeled crude cell lysates revealed two bands of 47 and 53 kD. The 53 kD protein was enriched in the soluble fraction, while the 47 kD protein, which corresponded to the predicted molecular weight, was located primarily in the membrane fraction. Simultaneous overexpression of EP-R and TKA-1 cDNA, and subsequent immunoprecipitation of EP-R with MAb 108.1 resulted in selective coprecipitation of the 47 kD TKA-1 protein, indicating that the 53 kD protein does not interact with the receptor. Transfection of the TKA-1 expression plasmid alone and subsequent immunoprecipitation with MAb 108.1 yielded no band corresponding to TKA-1, clearly demonstrating that precipitation described immediately above was mediated exclusively by the EP-R, while immunoprecipitation of TKA-1 from nontransfected 293 cells revealed a faint band of 47 kD, demonstrating that 293 cells express endogenous TKA-1. The same band was detected in immunoblots with anti-TKA-1 antiserum.

To further investigate the identity of the 47 and 53 kD bands precipitating from transiently transfected 293 cell lysates, we used total cell extracts from nontransfected 293, A172 (ATCC# CRL 1620), T47D (ATCC# HTB 133), HBL-100 (ATCC# HTB 124), MCF-7 (ATCC# GTB 22), and SK-BR-3 (ATCC# HTB 30) cells and tested for TKA-1 expression by Western blot analysis using affinity-purified TKA-1 antibodies. In all human cell lines, only the 47 kD TKA-1 form was detected, which migrated as a diffuse band of varying intensity. This suggested that transient overexpression in 293 cells resulted in a currently unknown covalent modification of a fraction of newly synthesized TKA-1.

EXAMPLE 4

TKA-1 interacts specifically with the C-terminus of the PDGF-β receptor

To determine functional characteristics of TKA-1, various RTKs and RTK mutants were overexpressed with and without TKA-1. After metabolic labeling of the cells with [$^{35}$S]methionine, the receptors were immunoprecipitated with monoclonal antibody 108.1 against the EGF-R extracellular domain present in all the receptors used. Binding of TKA-1 was determined by coimmunoprecipitation of the 47 kD form.

In a first set of experiments, EP-R, CSF-1-R, and EK-R expression vectors (an EGF-R/kit chimera, Herbst, R. et al., (1991), *J. Biol. Chem.,* 266:19908–19916) were transfected alone or together with the TKA-1 expression plasmid into 293 fibroblasts.

In particular, 293 cells were transiently transfected with receptor expression plasmid and simultaneously with receptor and TKA-1 expression plasmids. Cells were metabolically labeled with [$^{35}$S]methionine, after which lysates were prepared and RTKs immunoprecipitated with 108.1 (EP-R and EK-R) or CSF-1 receptor-specific antibodies. The immunoprecipitated proteins were separated on a 7.5% SDS-PAGE gel. Autoradiography was performed overnight.

Only immunoprecipitation of EP-R resulted in coimmunoprecipitation of TKA-1, demonstrating that the closely related CSF-1-R and kit receptor cytoplasmic domains do not mediate binding of TKA-1. The human EGF-R (HER), HER2, and insulin cytoplasmic domains were also found to be binding-negative, indicating that TKA-1 binds specifically to the PDGF-R. In a similar experiment we found that both α and β PDGF-R interacted with similar affinity with TKA-1.

In a third set of experiments, we investigated the binding of TKA-1 to the wild type (EP-R) and various PDGF-R cytoplasmic domain deletion mutants, including EP-RD83, lacking 83 amino acids of the kinase insertion sequence, EP-RD103, lacking the entire kinase insertion sequence, and three progressive C-terminal deletion mutants lacking 74 (EP-RDCT74), 80 (EP-RDCT80), and 115 (EP-RDCT115) amino acids (Seedorf et al., 1992).

In particular, 293 cells were transiently transfected with EP-R, EP-RD83 (lacking 83 amino acids of the PDGF-R kinase insertion sequence (KIS)), EP-RD103 (lacking the entire KIS), EP-RDCT74, EP-RDCT80, and EP-RDCT115 (lacking the PDGF-R C-terminal-most 74, 80, and 115 amino acids, respectively), expression plasmid alone or together with TKA-1 expression plasmid. Cells were further treated and after immunoprecipitation of the receptors with MAb 108.1, the proteins were separated on a 7.5% SDS-PAGE gel and exposed to X-ray film.

The kinase insertion mutants mediated normal binding of TKA-1, while all C-terminal truncation mutants lost their ability to coimmunoprecipitate this protein. These data indicate that the C-terminal-most 74 amino acids contain the TKA-1 binding site and, because EP-RD103 is autophosphorylation-negative, that receptor autophosphorylation is not required.

EXAMPLE 5

TKA-1 activates ligand-independent receptor phosphorylation on tyrosine

A potential role in signal regulation for TKA-1 was first examined by determining the effects of TKA-1 on EP-R autophosphorylation and receptor-mediated substrate phosphorylation in transiently overexpressing 293 fibroblasts. Cells were transfected with TKA-1, EP-R, or EP-R+TKA-1, starved for 24 hours in medium containing 0.5% FCS, and subsequently left untreated or treated with EGF for 10 minutes. After lysis in SDS-containing buffer, cell proteins were separated by SDS-PAGE and transferred to nitrocellulose. Immunoblotting with antiphosphotyrosine-specific antibodies revealed strong EP-R and substrate phosphorylation upon EGF addition (exposure time was 1 minute using horseradish peroxidase coupled second antibodies and ECL (Amersham)). Coexpression of TKA-1 stimulated receptor and substrate phosphorylation in the absence of EGF, whereas EGF treatment and TKA-1 coexpression appeared to have additive effects. Expression of TKA-1 in the absence of EP-R caused no protein tyrosine phosphorylation, demonstrating that substrate phosphorylation was mediated exclusively by the activated EP-R. Expression levels of both EP-R and TKA-1 were comparable in relevant samples.

Our data indicated that TKA-1 was able to partially activate PDGF-R kinase activity by binding to receptor C-tail sequences. To extend this observation, we examined the activation of receptor-bound PI3K. 293 cells were transfected as before (i.e., untransfected, transfected with EP-R, or EP-R and TKA-1 expression plasmids) and metabolically labeled with [$^{35}$S]methionine overnight in the presence of 0.5% FCS. After stimulation with EGF for 10 minutes, EP-R was immunoprecipitated with MAb 108.1. From each immunoprecipitate, three equal aliquots were prepared to test the amounts of EP-R and coimmunoprecipitation of TKA-1, to determine the phosphotyrosine state of the receptor by immunoblotting with antiphosphotyrosine antibody, and to measure receptor-bound PI-3-kinase activity. Two sets of aliquots were separated on 7.5% SDS-PAGE gels, from which one was directly exposed to X-ray film, while the other was subjected to Western blot analysis using antiphosphotyrosine-specific antibody 5E2. The third set of aliquots was used to determine the amount of PI-3-kinase activity that coimmunoprecipitated with EP-R. The PIP spots were scraped from TLC plates and analyzed by Cerenkov counting (C−: 20 cpm, C+: 25 cpm, EP-R-: 315 cpm, EP-R+: 945 cpm, EP-R TKA-1-: 1045 cpm, EP-R TKA-1+: 1630 cpm).

Approximately equal amounts of EP-R were immunoprecipitated and that in cells that coexpressed TKA-1, immunoprecipitation of the receptor resulted in coimmunoprecipitation of TKA-1. Moreover, coexpression of TKA-1 resulted in activation of EP-R autophosphorylation in the absence of ligand and in binding of active PI3K. The extent of TKA-1 binding-induced, receptor-bound PI3K activity was almost identical to that induced by ligand activation of the receptor in the absence of TKA-1 (1045 cpm versus 945 cpm).

EXAMPLE 6

Stable expression of TKA-1 in NIH3T3 fibroblasts

For stable expression in NIH3T3 fibroblasts, the TKA-1 cDNA was cloned into an SV40 promoter-driven expression vector. After transfection and selection with G418, several clones were isolated 14 days later and TKA-1 expression was determined by Western blot analysis using TKA-1-specific antisera.

Using TKA-1-specific antibodies, several clones expressing TKA-1 at different levels were identified. The apparent molecular weight of TKA-1 expressed in NIH 3T3 transfectants matched that of the endogenous protein in 293 and SK-BR-3 cells, which further confirmed that the 47 kD band of transfected 293 cells corresponds to the native form. Nontransfected NIH3T3 cells did not show a band corresponding to TKA-1, possibly due to a lack of crossreactivity of the antiserum with the mouse homolog.

In order to determine possible changes in the mitogenic response of NIH3T3/TKA-1 transfectants to PDGF, eight randomly selected clones were pooled and compared with nontransfected NIH3T3 cells. [$^3$H]thymidine incorporation into DNA was determined as described herein. Equal amounts of NIH3T3 cells and a pool of 8 randomly selected TKA-1-expressing NIH3T3 cells were incubated for 18 hours in the presence of increasing concentrations of PDGF. [$^3$H]thymidine was added for 4 hours and trichloroacetic acid-precipitable radioactivity was determined. The average of two independent experiments was used for analysis.

TKA-1-expressing NIH3T3 cells displayed enhanced sensitivity to PDGF in a $^3$H-thymidine incorporation assay. The basal level of DNA synthesis in serum-starved cells was about 3 times higher than in cells expressing TKA-1. This level was reached in NIH3T3 cells only with 2 ng/ml PDGF, indicating that TKA-1 activated the endogenous PDGF-R in a ligand-in dependent fashion.

EXAMPLE 7

TKA-1 promotes reorganization of actin cables

The effect of PDGF stimulation and TKA-1 expression on actin reorganization, as visualized by staining with TRITC-labeled phalloidin, was examined in NIH3T3 and NIH3T3/TKA-1 cells.

Serum-starved NIH3T3 cells and TKA-1-expressing NIH3T3 cells were fixed with either no addition, stimulation with 5 ng/ml PDGF for 10 min, 30 min (E and F), or 60 min, and stained with TRITC-labeled phalloidin to show actin filaments. Serum-starved NIH3T3 cells exhibited diffuse actin circles and actin stress fibers which, upon PDGF stimulation for 10 minutes, disappeared and reorganized in edge ruffles. Prolonged incubation with PDGF resulted in partial reappearance of stress fibers, indicating that this was a transient effect. In contrast, NIH3T3 cells stably expressing TKA-1 displayed no actin stress fibers after serum starvation. Actin is diffusely organized in small circles within the cytoplasma and in minor edge ruffles, which upon PDGF stimulation became reorganized in pronounced ruffles and microspikes. Prolonged incubation with PDGF resulted in the disappearance of microspikes and the reappearance of small actin circles around the nucleus, but prevented the regeneration of stress fibers.

EXAMPLE 8

In Vitro Assay

The following protocol describes the procedures used to identify substances that interfere with the binding between a GLGF domain containing protein and a PDGF-R in an ELISA format.

REAGENTS AND SUPPLIES:

1. Corning 96-well Elisa plates Corning Catalog #25805-96
2. Anti β PDGF-R monoclonal antibody Genzyme (Cambridge, Mass. catalog number 1263-00
3. PBS (Dulbecco's Phosphate-Buffered Saline) Gibco Catalog #450-1300EB Formulation: 2.7mM KCL
1.1 mM MgC12 (anhydrous)
138 mM NaCl
8.1 mN $Na_2HPO_4$ 4. TBST Buffer Formulation: 50 mM Tris pH7.2
150 mM NaCl
0.1% Triton X-100

5. Blocking Buffer

Formulation: 5% Carnation Instant Milk in TBST

6. PDGF-R expressing cells such as 293 cells engineered to express PDGF-R and TKA-1.
7. HNTG* Buffer Formulation: 50mM HEPES pH7.5
150 mN NaCl
10% Glycerol
1% Triton X 100
1 mM Sodium vanadate
2 mM EDTA
5 mM Sodium pyrophosphate
1 mM PMSF

8. TBST+1% DMSO

Formulation: 1% DMSO in TBST Buffer
(DMSO from Sigma, Catalog #2650)

9. NUNC 96-well V bottom polypropylene plates Applies Scientific Catalog # AS-72092
10. Purified TKA-1 antibody
11. Goat anti-rabbit IgG peroxidase conjugate BioSource International (Camarillo, Calif.) Catalog # NR5430, Lot # 2103. Stored in Enzymology Lab, SUGEN, Inc., −20 C., 1 ml aliquots. Thaw aliquot once and leave a 4 C. for 4 weeks.

12. ABTS Solution

Formulation: 100 mM Citric Acid (anhydrous), 250 mM Na2HPO4 pH 4.0, 0.5 mg/ml ABTS (2,2'-azzino-bis (3-ethylbenzthiazoline-6-sulfonic acid), (Sigma Catalog # A-1888) Keep solution in dark at 4 C. until ready to use.

13. Hydrogen peroxide 30% solution, Fisher Catalog #H325, store in the dark at 4 C. until ready to use.

14. ABTS/H202

Formulation: 15 mls ABTS solution, add 2 ul H202

Prepare 5 minutes before use and leave at room temperature.

15. Purified TKA-1 protein

EXAMPLE 9

Procedure

1. Coat Corning 96-well ELISA plates with 0.5 ug anti-PDGFR monoclonal antibody. Bring final volume to 100 ul per well with PBS. Coat plates overnight at 4 C.

2. Remove unbound antibody from wells by inverting plate to remove the liquid. Wash 4×with TBST by filling wells and inverting plate between each wash. Pat the plate on a paper towel to remove excess liquid and bubbles.

3. Block plates with 5% milk in TBST, 150 ul per well. Incubate plate 30 minutes while shaking on a microtiter plate shaker.

4. Wash plate as described in step 2.

5. Grow cells to 80–90% confluency. Wash the cells 2×with PBS and lyse the cells in HNTG* buffer. Remove insoluble material by centrifugation (10,000×g, 10 min at 4 degree C.) and aliquot the lysate. Store the lysate at minus 80 degrees C. Add approximately 50 ul cell lysate per well.

6. Wash 4×as described in step 2.

7. Dilute test substances 200 to 0.1 uM in 1% DMSO in 100 ul TBST and add concurrently with purified TKA-1 protein. Pre-incubated test substance and TKA-1 protein to wells containing the ELISA plate immobilized PDGF-R. Shake for 30 minutes.

8. After pre-incubation add 150 ul of the pre-incubated test substance and TKA-1 protein to wells containing the ELISA plate immobilized PDFG-R. Shake for 30 minutes.

9. Wash as described in step 2.

10. Dilute the anti-TKA-1 antiserum in TBST. Add 150 ul per well. Shake for 30 minutes.

11. Wash as described in step 2.

12. Dilute Goat anti-rabbit IgG-conjugated horseradish peroxidase approximately 1:2500 in TBST. Add 150 ul per well. Incubate 30 minutes while shaking.

13. Wash as described in step 2 and rinse twice with distilled water. Aspirate the liquid.

14. Add 100 ul of ABTS/H202 solution to well. Incubate 10 minutes while shaking.

15. Remove bubbles with slow stream of air.

16. Read plate on Dynatech MR5000 ELISA reader.

Test Filter: 410 nM

Reference Filter: 630 nM

A similar assay can be used to identify substances that interfere with the binding between PDGF-R and TKA-1. Assay plates are prepared as described in the previous protocol. Cells that express both proteins, such as the genetically engineered 293 cells described herein, are grown to 80–90% confluency then collected by trypsinization (0.25% trypsin-EDTA (Gibco)). The reaction is stopped with the addition of medium containing 10% fetal calf serum. The cells are suspended in fresh medium, and centrifuged once at 1500 rpm, rt, for 5 minutes. The cells are resuspended in fresh medium and transferred to 96 well tissue culture plates (10,000–5,000 cells per well) in about 100 $\mu$l per will. The plates are then incubated at 37 degrees in 5% $CO_2$ overnight.

Media in the wells is replaced by serum free growth media, 90 $\mu$l per well. Serial dilutions of test substance stocks (10 mg/ml) are diluted 1:10 into growth media and 10 $\mu$l added per well for a final concentration range of 100 $\mu$M to 1 nM. Control wells receive DMSO and medium only. The cells are incubated from 30 minutes to 2 hours at 37 degrees C., 5% $CO_2$.

After incubation, the cells are washed twice with PBS and lysed as previously described. The cells are scraped from the microtiter wells and homogenized using a pipette tip and repeated aspirating and dispensing. The lysate is transferred to the previously prepared assay plate wells and allowed to bind for 1 hour at room temperature, shaking. The lysate is removed and the plate washed 4 time with TBST.

The ability of the test substance to interfere with binding can be measured directly using and anti TKA-1 antibody as previously described. Alternatively, as TKA-1 binding has ben shown to cause autophosphorylation of the PDGF-receptor, one can measure the amount of phosphotyrosine present on the bound PDFG-receptors. This can be done by the addition of anti-PY (rabbit polyclonal antiphosphotyrosine antibody prepared according the Fendly, et al., 1990, *Cancer Research* 50: 1550–1558) at 100 $\mu$l per well, diluted with TBST, then incubated, shaking, at room temperature for 30 minutes. The anti-PY solution is removed, and the plate washed 4 time with TBST. The amount of antibody bound is detected in the same manner as previously described.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and non-patent references, are expressly incorporated herein by reference for all purposes.

Other embodiments are within the following claims.

What is claimed is:

1. An isolated, enriched or purified nucleic acid molecule, comprising (a) a nucleotide sequence encoding a polypeptide that differs from the polypeptide having the amino acid sequence as set forth in SEQ ID No:2 in that it lacks at least one, but not all, of the following segments of amino acid residues: 7–89, 7–112, 146–229, or 146–252; or (e) the complement of the nucleotide sequence of (a).

2. The nucleic acid molecule of claim 1, wherein said nucleotide sequence encodes a polypeptide that differs from the polypeptide having the amino acid sequence as set forth in SEQ ID NO:2 in that it lacks one of the following segments of amino acid residues: 7–89 or 146–229.

3. An isolated, enriched or purified nucleic acid molecule, comprising (a) a nucleotide sequence that encodes a polypeptide, free from other polypeptides normally associated with it in a naturally occurring cell, having an amino acid sequence set forth in SEQ ID NO:2 from amino acid residues 7–89, 7–112, 146–229, or 146–252; or (b) the complement of the nucleotide sequence of (a).

4. The nucleic acid molecule of claim 1, 2, or 3, wherein said nucleic acid molecule is cDNA.

5. A recombinant nucleic acid comprising a nucleic acid molecule of claim 1, 2 or 3.

6. An expression vector comprising a nucleic acid molecule of claim 1, 2 or 3 operably linked to a regulatory nucleotide sequence that controls expression of the nucleic acid molecule in a host cell.

7. An isolated host cell transfected or transformed with a nucleic acid molecule of claim 1, 2 or 3.

8. An isolated host cell transfected or transformed with a nucleic acid molecule of claim 1, 2 or 3 said nucleic acid molecule operably linked to a regulatory nucleotide sequence that controls expression of the nucleic acid molecule in said host cell.

9. The host cell of claim 8 in which said host cell is a mammalian host cell.

* * * * *

SEQUENCE LISTING

```
(1) GENERAL INFORMATION:

   (iii) NUMBER OF SEQUENCES:        2


(2) INFORMATION FOR SEQ ID NO:1:

     (i) SEQUENCE CHARACTERISTICS:
          (A) LENGTH:                1642 base pairs
          (B) TYPE:                  nucleic acid
          (C) STRANDEDNESS:          single
          (D) TOPOLOGY:              linear
```

```
    (ix) FEATURE:
          (A) NAME/KEY: Coding Sequence
          (B) LOCATION: 97...1446

    (xi) SEQUENCE DESCRIPTION: SEQ ID NO:1:

GCCGCCGCTG AAGCCACCGC CGGGTGCCCA GCGCCGCCGC CGCCCCCGAG CTCCCCCGCG      60

CCCCTGCCCG CGGGCGGCCG GTGGGCAGCG GGCGCC ATG GCC GCG CCG GAG CCG      114
                                        Met Ala Ala Pro Glu Pro
                                         1               5

CTG CGG CCG CGC CTG TGC CGC TTG GTG CGC GGA GAG CAG GGC TAC GGC      162
Leu Arg Pro Arg Leu Cys Arg Leu Val Arg Gly Glu Gln Gly Tyr Gly
            10                  15                  20

TTC CAC CTG CAC GGC GAG AAG GGC CGC CGC GGG CAG TTC ATC CGG CGC      210
Phe His Leu His Gly Glu Lys Gly Arg Arg Gly Gln Phe Ile Arg Arg
        25                  30                  35

GTG GAA CCC GGT TCC CCC GCC GAG GCC GCC GCG CTG GCT GGG GAC CGC      258
Val Glu Pro Gly Ser Pro Ala Glu Ala Ala Ala Leu Ala Gly Asp Arg
    40                  45                  50

CTG GTC GAG GTC AAC GGC GTC AAC GTG GAG GGC GAG ACG CAC CAC CAG      306
Leu Val Glu Val Asn Gly Val Asn Val Glu Gly Glu Thr His His Gln
55                  60                  65                  70

GTG GTG CAA AGG ATC AAG GCT GTG GAG GGG CAG ACT CGG CTG CTG GTG      354
Val Val Gln Arg Ile Lys Ala Val Glu Gly Gln Thr Arg Leu Leu Val
                75                  80                  85

GTG GAC CAG GAG ACA GAT GAG GAG CTC CGC CGG CGG CAG CTG ACC TGT      402
Val Asp Gln Glu Thr Asp Glu Glu Leu Arg Arg Arg Gln Leu Thr Cys
            90                  95                  100

ACC GAG GAG ATG GCC CAG CGA GGG CTC CCA CCC GCC CAC GAC CCC TGG      450
Thr Glu Glu Met Ala Gln Arg Gly Leu Pro Pro Ala His Asp Pro Trp
        105                 110                 115

GAG CCG AAG CCA GAC TGG GCA CAC ACC GGC AGC CAC AGC TCC GAA GCT      498
Glu Pro Lys Pro Asp Trp Ala His Thr Gly Ser His Ser Ser Glu Ala
    120                 125                 130

GGC AAG AAG GAT GTC AGT GGG CCC CTG AGG GAG CTG CGC CCT CGG CTC      546
Gly Lys Lys Asp Val Ser Gly Pro Leu Arg Glu Leu Arg Pro Arg Leu
135                 140                 145                 150

TGC CAC CTG CGA AAG GGA CCT CAG GGC TAT GGG TTC AAC CTG CAT AGT      594
Cys His Leu Arg Lys Gly Pro Gln Gly Tyr Gly Phe Asn Leu His Ser
                155                 160                 165

GAC AAG TCC CGG CCC GGC CAG TAC ATC CGC TCT GTG GAC CCG GGC TCA      642
Asp Lys Ser Arg Pro Gly Gln Tyr Ile Arg Ser Val Asp Pro Gly Ser
            170                 175                 180

CCT GCC GCC CGC TCT GGC CTC CGC GCC CAG GAC CGG CTC ATT GAG GTG      690
Pro Ala Ala Arg Ser Gly Leu Arg Ala Gln Asp Arg Leu Ile Glu Val
        185                 190                 195

AAC GGG CAG AAT GTG GAG GGA CTG CGC CAT GCT GAG GTG GTG GCC AGC      738
Asn Gly Gln Asn Val Glu Gly Leu Arg His Ala Glu Val Val Ala Ser
    200                 205                 210

ATC AAG GCA CGG GAG GAC GAG GCC CGG CTG CTG GTC GTG GAC CCC GAG      786
Ile Lys Ala Arg Glu Asp Glu Ala Arg Leu Leu Val Val Asp Pro Glu
215                 220                 225                 230

ACA GAT GAA CAC TTC AAG CGG CTT CGG GTC ACA CCC ACC GAG GAG CAC      834
Thr Asp Glu His Phe Lys Arg Leu Arg Val Thr Pro Thr Glu Glu His
                235                 240                 245

GTG GAA GGT CCT CTG CCG TCA CCC GTC ACC AAT GGA ACC AGC CCT GCC      882
Val Glu Gly Pro Leu Pro Ser Pro Val Thr Asn Gly Thr Ser Pro Ala
            250                 255                 260

CAG CTC AAT GGT GGC TCT GCG TGC TCA TCC CGA AGT GAC CTG CCT GGT      930
Gln Leu Asn Gly Gly Ser Ala Cys Ser Ser Arg Ser Asp Leu Pro Gly
        265                 270                 275
```

```
TCC GAC AAG GAC ACT GAG GAT GGC AGT GCC TGG AAG CAA GAT CCC TTC      978
Ser Asp Lys Asp Thr Glu Asp Gly Ser Ala Trp Lys Gln Asp Pro Phe
    280                 285                 290

CAG GAG AGC GGC CTC CAC CTG AGC CCC ACG GCG GCC GAG GCA AGG AGA     1026
Gln Glu Ser Gly Leu His Leu Ser Pro Thr Ala Ala Glu Ala Arg Arg
295                 300                 305                 310

AGG CTC GAG CCA TGC GAG TCA ACA AGC GCG CGC CAC AGA TGG ACT GGA     1074
Arg Leu Glu Pro Cys Glu Ser Thr Ser Ala Arg His Arg Trp Thr Gly
                315                 320                 325

ACA GGA AGC GTG AAA TCT TCA GCA ACT TCT GAG CCC CTT CCT GCC TGT     1122
Thr Gly Ser Val Lys Ser Ser Ala Thr Ser Glu Pro Leu Pro Ala Cys
            330                 335                 340

CTC GGG ACC CTG GGA CCC CTC CCG CAC GGA CCT TGG GCC TCA GCC TGC     1170
Leu Gly Thr Leu Gly Pro Leu Pro His Gly Pro Trp Ala Ser Ala Cys
        345                 350                 355

CCC GAG CTC CCC CAG CCT CAG TGG ACT GGA GGG TGG TCC TGC CAT TGC     1218
Pro Glu Leu Pro Gln Pro Gln Trp Thr Gly Gly Trp Ser Cys His Cys
    360                 365                 370

CCA GAA ATC AGC CCC AGC CCC GGT GAG CCC CCA TCC TGC CCC TGC CCA     1266
Pro Glu Ile Ser Pro Ser Pro Gly Glu Pro Pro Ser Cys Pro Cys Pro
375                 380                 385                 390

CCA GGT ACT GGG GGC CTG TGG CAG CAA GAT AGG GGG AGA GAG ACC CAG     1314
Pro Gly Thr Gly Gly Leu Trp Gln Gln Asp Arg Gly Arg Glu Thr Gln
                395                 400                 405

AGA TGT GAG AGA GAG TCA GAG ACA GAG ACA GAG AGA GAG AGA GAG AGA     1362
Arg Cys Glu Arg Glu Ser Glu Thr Glu Thr Glu Arg Glu Arg Glu Arg
            410                 415                 420

CAC AGA GAG AGA CAG AGA GAG AGC GAG CGA GCG CGC GGC AGC CGC GGG     1410
His Arg Glu Arg Gln Arg Glu Ser Glu Arg Ala Arg Gly Ser Arg Gly
        425                 430                 435

GCG AGG GCC TTT GCT GCT CTG CCG GGG CCT GCT GAC TGAAAGGAAT TTGTGTT  1463
Ala Arg Ala Phe Ala Ala Leu Pro Gly Pro Ala Asp
    440                 445                 450

TTTGCTTTTT TTCCAAAAAG ATCTCCAGCT CCACACATGT TTCCACTTAA TACCAGAGAC   1523

CCCCCCCTTC CCCTCCCCCT TCCCCTCCCC CTTGGGACGC GCTCTAAATA ATTGCAATAA   1583

AACAAACCTT TCTCTGCAAA AAAAAAAAAA AAAAAAAAAA AAAAAAAAAA AAAAAAAAA    1642
```

(2) INFORMATION FOR SEQ ID NO:2:

(i) SEQUENCE CHARACTERISTICS:
- (A) LENGTH: 450 amino acids
- (B) TYPE: amino acid
- (D) TOPOLOGY: linear (ii) MOLECULE TYPE: protein (xi) SEQUENCE DESCRIPTION: SEQ ID NO:2:

```
Met Ala Ala Pro Glu Pro Leu Arg Pro Arg Leu Cys Arg Leu Val Arg
 1               5                  10                  15

Gly Glu Gln Gly Tyr Gly Phe His Leu His Gly Glu Lys Gly Arg Arg
            20                  25                  30

Gly Gln Phe Ile Arg Arg Val Glu Pro Gly Ser Pro Ala Glu Ala Ala
        35                  40                  45

Ala Leu Ala Gly Asp Arg Leu Val Glu Val Asn Gly Val Asn Val Glu
    50                  55                  60

Gly Glu Thr His His Gln Val Val Gln Arg Ile Lys Ala Val Glu Gly
65                  70                  75                  80

Gln Thr Arg Leu Leu Val Val Asp Gln Glu Thr Asp Glu Glu Leu Arg
                85                  90                  95
```

-continued

```
Arg Arg Gln Leu Thr Cys Thr Glu Glu Met Ala Gln Arg Gly Leu Pro
            100                 105                 110

Pro Ala His Asp Pro Trp Glu Pro Lys Pro Asp Trp Ala His Thr Gly
        115                 120                 125

Ser His Ser Ser Glu Ala Gly Lys Lys Asp Val Ser Gly Pro Leu Arg
    130                 135                 140

Glu Leu Arg Pro Arg Leu Cys His Leu Arg Lys Gly Pro Gln Gly Tyr
145                 150                 155                 160

Gly Phe Asn Leu His Ser Asp Lys Ser Arg Pro Gly Gln Tyr Ile Arg
                165                 170                 175

Ser Val Asp Pro Gly Ser Pro Gly Ala Arg Ser Gly Leu Arg Ala Gln
            180                 185                 190

Asp Arg Leu Ile Glu Val Asn Gly Gln Asn Val Glu Gly Leu Arg His
        195                 200                 205

Ala Glu Val Val Ala Ser Ile Lys Ala Arg Glu Asp Glu Ala Arg Leu
    210                 215                 220

Leu Val Val Asp Pro Glu Thr Asp Glu His Phe Lys Arg Leu Arg Val
225                 230                 235                 240

Thr Pro Thr Glu Glu His Val Glu Gly Pro Leu Pro Ser Pro Val Thr
                245                 250                 255

Asn Gly Thr Ser Pro Ala Gln Leu Asn Gly Gly Ser Ala Cys Ser Ser
            260                 265                 270

Arg Ser Asp Leu Pro Gly Ser Asp Lys Asp Thr Glu Asp Gly Ser Ala
        275                 280                 285

Trp Lys Gln Asp Pro Phe Gln Glu Ser Gly Leu His Leu Ser Pro Thr
    290                 295                 300

Ala Ala Glu Ala Arg Arg Arg Leu Glu Pro Cys Glu Ser Thr Ser Ala
305                 310                 315                 320

Arg His Arg Trp Thr Gly Thr Gly Ser Val Lys Ser Ser Ala Thr Ser
                325                 330                 335

Glu Pro Leu Pro Ala Cys Leu Gly Thr Leu Gly Pro Leu Pro His Gly
            340                 345                 350

Pro Trp Ala Ser Ala Cys Pro Glu Leu Pro Gln Pro Gln Trp Thr Gly
        355                 360                 365

Gly Trp Ser Cys His Cys Pro Glu Ile Ser Pro Ser Pro Gly Glu Pro
    370                 375                 380

Pro Ser Cys Pro Cys Pro Pro Gly Thr Gly Gly Leu Trp Gln Gln Asp
385                 390                 395                 400

Arg Gly Arg Glu Thr Gln Arg Cys Glu Arg Glu Ser Glu Thr Glu Thr
                405                 410                 415

Glu Arg Glu Arg Glu Arg His Arg Glu Arg Gln Arg Glu Ser Glu Arg
            420                 425                 430

Ala Arg Gly Ser Arg Gly Ala Arg Ala Phe Ala Ala Leu Pro Gly Pro
        435                 440                 445

Ala Asp
    450
```